United States Patent
Dacquay et al.

(10) Patent No.: US 7,762,981 B2
(45) Date of Patent: Jul. 27, 2010

(54) TEMPERATURE RELEASE MECHANISM FOR INJECTION DEVICE

(75) Inventors: Bruno Dacquay, Irvine, CA (US); Cesario Dos Santos, Aliso Viejo, CA (US); Casey Lind, Irvine, CA (US)

(73) Assignee: Alcon Research, Ltd., Fort Worth, TX (US)

(*) Notice: Subject to any disclaimer, the term of this patent is extended or adjusted under 35 U.S.C. 154(b) by 91 days.

(21) Appl. No.: 11/762,844

(22) Filed: Jun. 14, 2007

(65) Prior Publication Data

US 2008/0097311 A1 Apr. 24, 2008

Related U.S. Application Data

(63) Continuation-in-part of application No. 11/435,906, filed on May 17, 2006, now abandoned.

(60) Provisional application No. 60/921,497, filed on Oct. 16, 2006.

(51) Int. Cl.
*A61M 31/00* (2006.01)

(52) U.S. Cl. .................. 604/67; 604/113; 604/218; 604/233; 604/291; 604/530; 604/531; 604/131; 604/95.05; 424/423

(58) Field of Classification Search .................. 604/67, 604/113, 218, 233, 291, 311, 530, 531, 131; 424/423

See application file for complete search history.

(56) References Cited

U.S. PATENT DOCUMENTS

| | | | |
|---|---|---|---|
| 1,252,614 A | 1/1918 | Pieper | |
| 3,089,815 A | 5/1963 | Lieb, et al. | |
| 3,466,752 A | * | 9/1969 | Braun .......................... 433/32 |
| 3,608,549 A | 9/1971 | Merrill | |

(Continued)

FOREIGN PATENT DOCUMENTS

EP 0348146 A1 12/1989

(Continued)

OTHER PUBLICATIONS

"Ultra™ 2800 Positive Displacement Dispenser"; 2004; EFD, Inc. Brochure XP 1104 vol. 11.10; 2 pages.

(Continued)

*Primary Examiner*—Nicholas D Lucchesi
*Assistant Examiner*—Scott Medway
(74) *Attorney, Agent, or Firm*—Kenneth D. Bassinger

(57) ABSTRACT

An ophthalmic injection device has a dispensing chamber housing, a plunger, an actuator for driving the plunger, a temperature control device, and a temperature release mechanism. The dispensing chamber housing has an inner surface and an outer surface. The inner surface partially defines a dispensing chamber for holding a quantity of a substance. The plunger is engaged with the inner surface of the dispensing chamber housing, is capable of sliding in the dispensing chamber housing, and is fluidly sealed to the inner surface of the dispensing chamber housing. The temperature control device at least partially surrounds the dispensing chamber housing and is capable of altering the temperature of the substance in the dispensing chamber. The temperature release mechanism is in a locked position when the substance is outside the proper temperature range and an unlocked position when the substance is in the proper temperature range.

10 Claims, 5 Drawing Sheets

U.S. PATENT DOCUMENTS

| | | | |
|---|---|---|---|
| 3,653,552 A * | 4/1972 | Ash | 222/146.5 |
| 3,892,537 A | 7/1975 | Gulati et al. | |
| 3,982,537 A | 9/1976 | Bucalo | |
| 4,007,742 A | 2/1977 | Banko | |
| 4,030,499 A | 6/1977 | Bucalo | |
| 4,054,138 A | 10/1977 | Bucalo | |
| 4,122,850 A | 10/1978 | Bucalo | |
| 4,184,510 A | 1/1980 | Murry et al. | |
| 4,246,932 A | 1/1981 | Raines | |
| 4,265,618 A | 5/1981 | Herskovitz et al. | |
| 4,357,136 A | 11/1982 | Herskovitz et al. | |
| 4,392,827 A | 7/1983 | Martin | |
| 4,474,752 A | 10/1984 | Haslam et al. | |
| 4,484,915 A | 11/1984 | Tartaglia | |
| 4,582,488 A | 4/1986 | Newman | |
| 4,684,344 A | 8/1987 | Brockway et al. | |
| 4,704,088 A | 11/1987 | Newman | |
| 4,713,446 A | 12/1987 | DeVore et al. | |
| 4,795,423 A | 1/1989 | Osterholm | |
| 4,830,855 A | 5/1989 | Stewart | |
| 4,992,045 A | 2/1991 | Beisel | |
| 5,066,276 A | 11/1991 | Wang | |
| 5,120,307 A | 6/1992 | Wang | |
| 5,170,779 A * | 12/1992 | Ginsberg | 601/161 |
| 5,328,481 A | 7/1994 | Wang | |
| 5,336,175 A | 8/1994 | Mames | |
| 5,360,413 A | 11/1994 | Leason et al. | |
| 5,368,582 A * | 11/1994 | Bertera | 604/295 |
| 5,370,630 A | 12/1994 | Smidebush et al. | |
| 5,476,511 A | 12/1995 | Gwon et al. | |
| 5,487,725 A | 1/1996 | Peyman | |
| 5,582,595 A | 12/1996 | Haber et al. | |
| 5,620,700 A | 4/1997 | Berggren et al. | |
| 5,743,886 A | 4/1998 | Lynn et al. | |
| 5,773,019 A | 6/1998 | Ashton et al. | |
| 5,783,205 A | 7/1998 | Berggren et al. | |
| 5,824,072 A | 10/1998 | Wong | |
| 5,860,949 A | 1/1999 | Chen | |
| 5,891,094 A * | 4/1999 | Masterson et al. | 604/113 |
| 5,928,663 A | 7/1999 | Peyman | |
| 5,984,889 A | 11/1999 | Christ et al. | |
| 6,139,571 A * | 10/2000 | Fuller et al. | 607/105 |
| 6,210,357 B1 | 4/2001 | Morris | |
| 6,254,572 B1 * | 7/2001 | Knipfer et al. | 604/151 |
| 6,270,343 B1 | 8/2001 | Martin | |
| 6,290,690 B1 | 9/2001 | Huculak et al. | |
| 6,364,865 B1 | 4/2002 | Lavi et al. | |
| 6,372,245 B1 | 4/2002 | Bowman et al. | |
| 6,375,638 B2 * | 4/2002 | Nason et al. | 604/132 |
| 6,413,245 B1 | 7/2002 | Yaacobi et al. | |
| 6,413,278 B1 * | 7/2002 | Marchosky | 623/17.16 |
| 6,419,656 B1 | 7/2002 | Vetter et al. | |
| 6,436,143 B1 | 8/2002 | Ross et al. | |
| 6,488,659 B1 | 12/2002 | Rosenman | |
| 6,520,930 B2 | 2/2003 | Critchlow et al. | |
| 6,585,700 B1 | 7/2003 | Trocki et al. | |
| 6,595,979 B1 | 7/2003 | Epstein et al. | |
| 6,635,267 B1 | 10/2003 | Miyoshi et al. | |
| 6,645,179 B1 | 11/2003 | Ishikawa et al. | |
| 6,691,977 B2 * | 2/2004 | Knebel et al. | 251/11 |
| 6,726,654 B2 | 4/2004 | Rosenman | |
| 6,929,619 B2 * | 8/2005 | Fago et al. | 604/67 |
| 6,940,209 B2 | 9/2005 | Henderson | |
| 6,960,192 B1 * | 11/2005 | Flaherty et al. | 604/181 |
| 6,991,457 B2 | 1/2006 | Kazen et al. | |
| 7,052,251 B2 * | 5/2006 | Nason et al. | 417/321 |
| 7,086,861 B2 * | 8/2006 | Pitz et al. | 433/90 |
| 7,128,727 B2 * | 10/2006 | Flaherty et al. | 604/131 |
| 7,176,030 B2 | 2/2007 | Faries, Jr. et al. | |
| 7,186,247 B2 * | 3/2007 | Ujhelyi et al. | 604/891.1 |
| 2001/0016710 A1 * | 8/2001 | Nason et al. | 604/153 |
| 2002/0055720 A1 | 5/2002 | Hohlfelder et al. | |
| 2003/0055380 A1 | 3/2003 | Flaherty | |
| 2003/0125665 A1 | 7/2003 | Rosenman | |
| 2003/0163099 A1 * | 8/2003 | Wermeling et al. | 604/275 |
| 2004/0039253 A1 | 2/2004 | Peyman et al. | |
| 2004/0052761 A1 | 3/2004 | Vernon et al. | |
| 2004/0133155 A1 | 7/2004 | Varner et al. | |
| 2004/0176720 A1 | 9/2004 | Kipfer | |
| 2004/0210200 A1 | 10/2004 | Gerondale et al. | |
| 2004/0231667 A1 | 11/2004 | Horton et al. | |
| 2004/0267202 A1 * | 12/2004 | Potter | 604/158 |
| 2005/0065477 A1 | 3/2005 | Jost | |
| 2005/0177137 A1 | 8/2005 | Kipfer | |
| 2006/0047250 A1 | 3/2006 | Hickingbotham et al. | |
| 2006/0224145 A1 * | 10/2006 | Gillis et al. | 604/891.1 |

FOREIGN PATENT DOCUMENTS

| | | |
|---|---|---|
| EP | 0398394 | 11/1990 |
| GB | 1551767 | 8/1979 |
| WO | WO 82/03761 A1 | 11/1982 |
| WO | WO 87/00029 A1 | 1/1987 |
| WO | WO 96/03978 A1 | 2/1996 |
| WO | WO 99/33853 A2 | 7/1999 |
| WO | WO 01/10482 A1 | 2/2001 |
| WO | WO 2006/050008 A1 | 5/2006 |

OTHER PUBLICATIONS

"Parker: Your Resource For Motion And Fluid Control Components, Systems and Solutions—System Solutions For Life Sciences"; 2003; Aurora Instruments, LLC Brochure; 8 pages.
U.S. Appl. No. 11/200,452, filed Aug. 9, 2005, Hopkins.
U.S. Appl. No. 11/435,906, filed May 17, 2005, Dacquay et al.
U.S. Appl. No. 11/486,870, filed Jul. 14, 2006, Marsh et al.

* cited by examiner

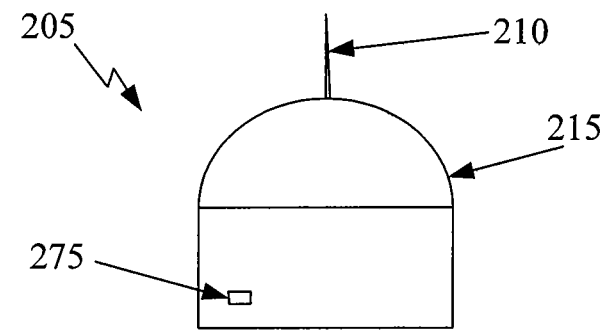
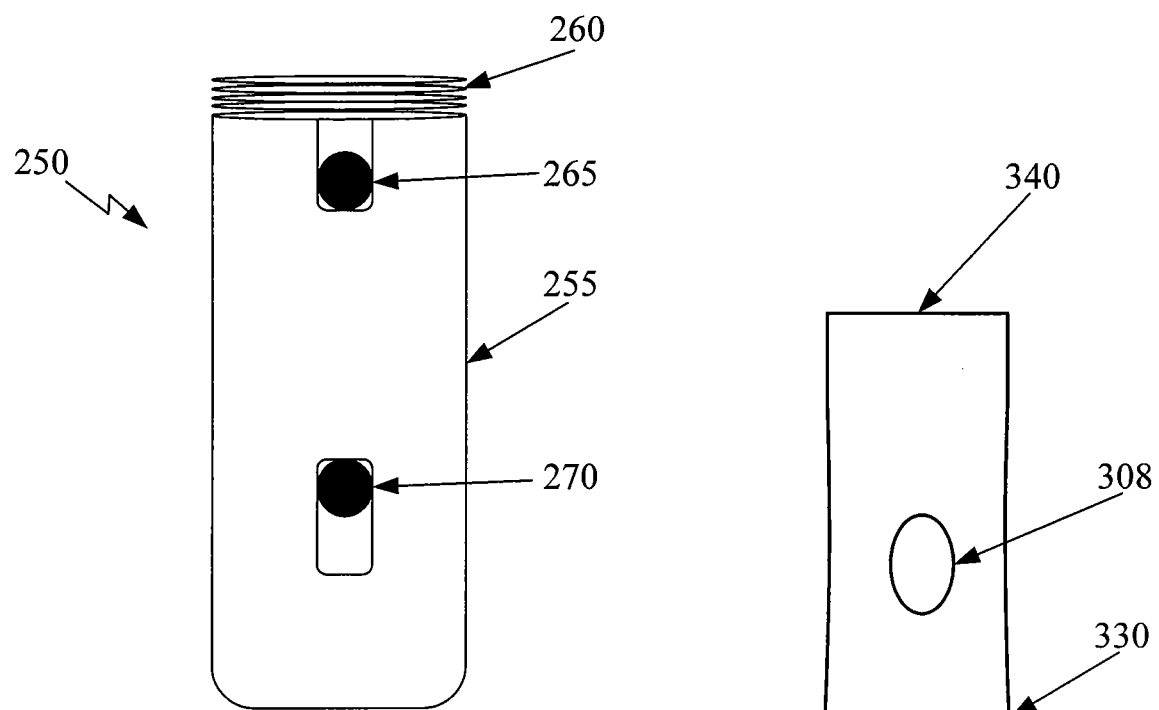
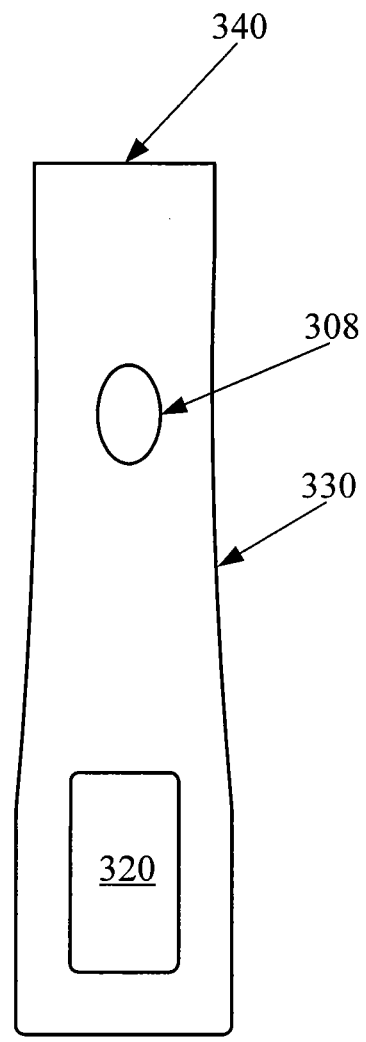
Fig. 2
Fig. 3

TEMPERATURE RELEASE MECHANISM FOR INJECTION DEVICE

RELATED APPLICATIONS

This Application claims priority to U.S. patent application Ser. No. 60/921,497 filed Oct. 16, 2006 and is a continuation-in-part of U.S. patent application Ser. No. 11/435,906 filed May 17, 2006 now abandoned.

BACKGROUND OF THE INVENTION

The present invention relates to a single-use medical device and more particularly to an ophthalmic drug delivery device with a temperature controlled delivery mechanism.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually made using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to puncture the eye tissue with the needle, hold the syringe steady, and actuate the syringe plunger (with or without the help of a nurse) to inject the fluid into the eye. The volume injected is typically not controlled in an accurate manner because the vernier on the syringe is not precise relative to the small injection volume. Fluid flow rates are uncontrolled. Reading the vernier is also subject to parallax error. Tissue damage may occur due to an "unsteady" injection. Reflux of the drug may also occur when the needle is removed from the eye.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. Ypsomed, Inc. of Switzerland produces a line of injection pens and automated injectors primarily for the self-injection of insulin or hormones by a patient. This product line includes simple disposable pens and electronically-controlled motorized injectors.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a portable hand piece for reliably injecting a drug into the eye. In the case where the drug is to be heated or cooled, it is desirable to bring the drug to the proper temperature before it is injected into the eye. A switch, button, or other mechanism that can only be activated when the drug reaches the proper temperature can be used to ensure that the drug is at the proper temperature before being injected. Such a system provides numerous benefits over prior art injectors.

SUMMARY OF THE INVENTION

In one embodiment consistent with the principles of the present invention, the present invention is an ophthalmic injection device having a dispensing chamber housing, a plunger, an actuator for driving the plunger, a temperature control device, a power source for providing power to the temperature control device, a controller for controlling the temperature control device, and a temperature release mechanism. The dispensing chamber housing has an inner surface and an outer surface. The inner surface partially defines a dispensing chamber for holding a quantity of a substance. The plunger is engaged with the inner surface of the dispensing chamber housing, is capable of sliding in the dispensing chamber housing, and is fluidly sealed to the inner surface of the dispensing chamber housing. The temperature control device at least partially surrounds the dispensing chamber housing and is capable of altering the temperature of the substance in the dispensing chamber. The temperature release mechanism activates the actuator only when the substance is in a proper temperature range.

In another embodiment consistent with the principles of the present invention, the present invention is an ophthalmic injection device having a dispensing chamber housing, a needle, a plunger, an actuator for driving the plunger, a temperature control device, a power source for providing power to the temperature control device, a controller for controlling the temperature control device, and a temperature release mechanism. The dispensing chamber housing has an inner surface and an outer surface. The inner surface partially defines a dispensing chamber for holding a quantity of a substance. The plunger is engaged with the inner surface of the dispensing chamber housing, is capable of sliding in the dispensing chamber housing, and is fluidly sealed to the inner surface of the dispensing chamber housing. The needle is fluidly coupled to the dispensing chamber. The temperature control device at least partially surrounds the dispensing chamber housing and is capable of altering the temperature of the substance in the dispensing chamber. The temperature release mechanism is in a locked position when the substance is outside the proper temperature range, and an unlocked position when the substance is in the proper temperature range.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 is one view of an ophthalmic medical device including a disposable tip segment and a limited reuse assembly according to an embodiment of the present invention.

FIG. 3 is another embodiment of a limited reuse assembly according to the principles of the present invention.

DETAILED DESCRIPTION OF THE PREFERRED EMBODIMENTS

Figure 1:
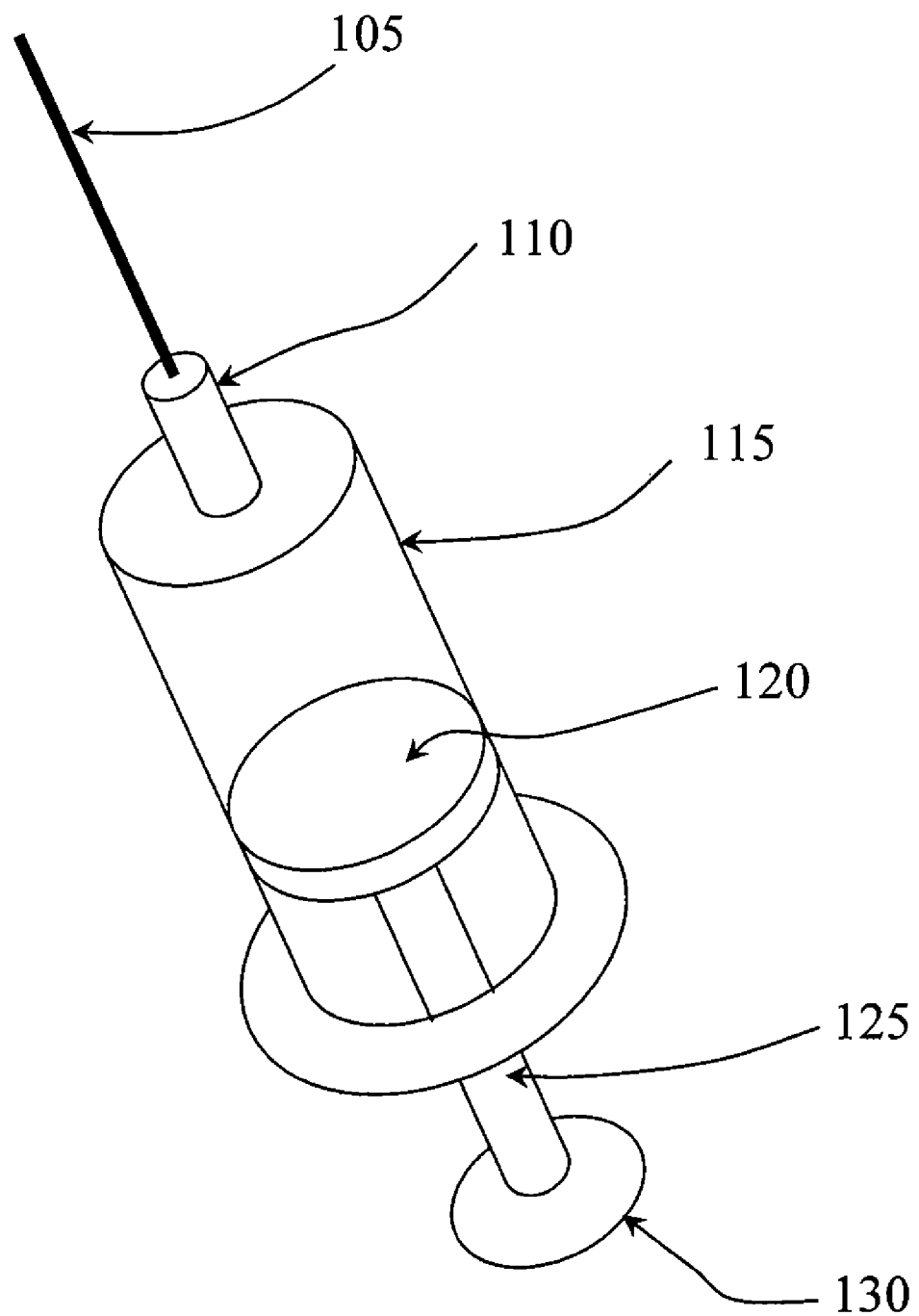
FIG. 1 is a perspective view of a prior art syringe.

Reference is now made in detail to the exemplary embodiments of the invention, examples of which are illustrated in the accompanying drawings. Wherever possible, the same reference numbers are used throughout the drawings to refer to the same or like parts.

FIG. 2 is one view of an ophthalmic medical device including a disposable tip segment and a limited reuse assembly according to an embodiment of the present invention. In FIG. 2, the medical device includes a tip segment 205 and a limited reuse assembly 250. The tip segment 205 includes a needle 210, a housing 215, and an optional light 275. The limited reuse assembly 250 includes a housing 255, a switch 270, a lock mechanism 265, and a threaded portion 260.

Tip segment 205 is capable of being connected to and removed from limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug.

Switch 270 is adapted to provide an input to the system. For example, switch 270 may be used to activate the system or to turn on a heater. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of disposable tip segment 205. For example, optional light 275 may also pulse on and off to indicate other states, such as, but not limited to a system error, fully charged battery, insufficiently charged battery or faulty connection between the tip segment 205 and limited use assembly 250. While shown on tip segment 205, optional light 275 or other indicator may be located on limited reuse assembly 250.

FIG. 3 is another embodiment of a limited reuse assembly according to the principles of the present invention. Limited reuse assembly 250 includes a button 308, a display 320, and a housing 330. Disposable tip segment 205 attaches to end 340 of limited reuse assembly 250. Button 308 is actuated to provide an input to the system. As with switch 270, button 308 may activate a heater or other temperature control device or initiate actuation of a plunger. Display 320 is a liquid crystal display, segmented display, or other device that indicates a status or condition of disposable tip segment 205 or limited reuse assembly 250.

Figure 4:
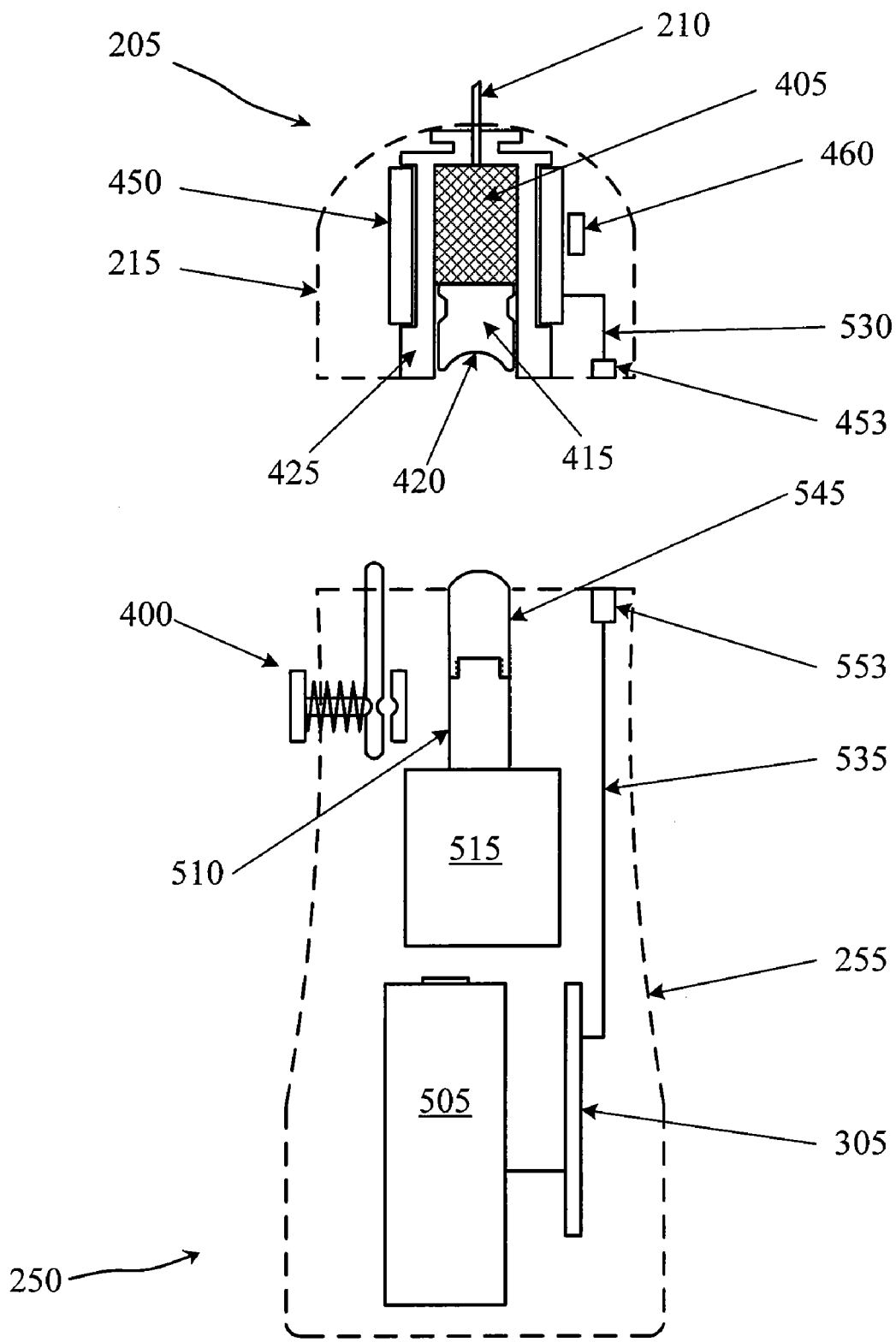
FIG. 4 is a cross section view of a disposable tip segment and a limited reuse assembly according to an embodiment of the present invention.

FIG. 4 is a cross section view of a disposable tip segment and a limited reuse assembly according to an embodiment of the present invention. FIG. 4 shows how tip segment 205 interfaces with limited reuse assembly 250. In the embodiment of FIG. 4, tip segment 205 includes plunger interface 420, plunger 415, dispensing chamber housing 425, tip segment housing 215, temperature control device 450, thermal sensor 460, needle 210, dispensing chamber 405, interface 530, and tip interface connector 453. Limited reuse assembly 250 includes mechanical linkage interface 545, actuator shaft 510, actuator 515, power source 505, controller 305, limited reuse assembly housing 255, temperature release mechanism 400, interface 535, and limited reuse assembly interface connector 553.

In tip segment 205, plunger interface 420 is located on one end of plunger 415. The other end of plunger 415 forms one end of dispensing chamber 405. Plunger 415 is adapted to slide within dispensing chamber 405. The outer surface of plunger 415 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape.

Needle 210 is fluidly coupled to dispensing chamber 405. In such a case, a substance contained in dispensing chamber 405 can pass through needle 210 and into an eye. Temperature control device 450 at least partially surrounds dispensing chamber housing 425. In this case, temperature control device 450 is adapted to heat and/or cool dispensing chamber housing 425 and any substance contained in dispensing chamber 405. Interface 530 connects temperature control device 450 with tip interface connector 453.

Optional thermal sensor 460 provides temperature information to assist in controlling the operation of temperature control device 450. Thermal sensor 460 may be located near dispensing chamber housing 425 and measure a temperature near dispensing chamber housing 425 or may be located in thermal contact with dispensing chamber housing 425, in which case it measures a temperature of dispensing chamber housing 425. Thermal sensor 460 may be any of a number of different devices that can provide temperature information. For example, thermal sensor 460 may be a thermocouple or a resistive device whose resistance varies with temperature. Thermal sensor 460 is also electrically coupled to interface 530 or other similar interface.

The components of tip segment 205, including dispensing chamber housing 425, temperature control device 450, and plunger 415 are at least partially enclosed by tip segment housing 215. In one embodiment consistent with the principles of the present invention, plunger 415 is sealed to the interior surface of dispensing chamber housing 425. This seal prevents contamination of any substance contained in dispensing chamber 405. For medical purposes, such a seal is desirable. This seal can be located at any point on plunger 415 or dispensing chamber housing 425.

In limited reuse assembly 250, power source 505 provides power to actuator 515. An interface (not shown) between power source 505 and actuator 515 serves as a conduit for providing power to actuator 515. Actuator 515 is connected to actuator shaft 5 10. When actuator 515 is a stepper motor, actuator shaft 510 is integral with actuator 515. Mechanical linkage interface 545 is connected to actuator shaft 510. In this configuration, as actuator 515 moves actuator shaft 510 upward toward needle 210, mechanical linkage interface 545 also moves upward toward needle 210. In other embodiments of the present invention, mechanical linkage interface 545 and actuator shaft 510 are a single component. In other words, a shaft connected to actuator 515 includes both actuator shaft 510 and mechanical linkage interface 545 as a single assembly.

In limited reuse assembly 250, power source 505 is typically a rechargeable battery, such as a lithium ion battery, although other types of batteries may be employed. In addition, any other type of power cell is appropriate for power source 505. Power source 505 provides current to dispensing chamber housing 425 to heat/cool it and change its shape. Optionally, power source 505 can be removed from housing 255 through a door or other similar feature (not shown).

Controller 305 is connected via interface 535 to limited reuse assembly interface connecter 553. Limited reuse assembly interface connecter 553 is located on a top surface of limited reuse assembly housing 255 adjacent to mechanical linkage interface 545. In this manner, both limited reuse assembly interface connector 553 and mechanical linkage interface 545 are adapted to be connected with tip interface connector 453 and plunger interface 420, respectively.

Controller 305 and actuator 515 are connected by an interface (not shown). This interface (not shown) allows controller 305 to control the operation of actuator 515. In addition, an interface between power source 505 and controller 305 allows controller 305 to control operation of power source 505. In such a case, controller 305 may control the charging and the discharging of power source 505 when power source 505 is a rechargeable battery.

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control a temperature control device. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component in FIG. 4, controller 305 may be made of many different components or integrated circuits.

Limited reuse assembly 250 also includes temperature release mechanism 400. Temperature release mechanism 400 allows actuator 515 to be activated to deliver the substance only when the substance is in the proper temperature range. Temperature release mechanism 400 and its operation are more fully described below.

Tip segment 205 is adapted to mate with or attach to limited reuse assembly 250. In the embodiment of FIG. 4, plunger interface 420 located on a bottom surface of plunger 415 is adapted to mate with mechanical linkage interface 545 located near a top surface of limited reuse assembly housing 255. In addition, tip interface connector 453 is adapted to connect with limited reuse assembly interface connector 553. When tip segment 205 is connected to limited reuse assembly 250 in this manner, actuator 515 and actuator shaft 510 are adapted to drive plunger 415 upward toward needle 210. In addition, an interface is formed between controller 305 and temperature control device 450. A signal can pass from controller 305 to temperature control device 450 through interface 535, limited reuse assembly interface connector 553, tip interface connector 453, and interface 530.

In operation, when tip segment 205 is connected to limited reuse assembly 250, controller 305 controls the operation of actuator 515. Actuator 515 is activated by temperature release mechanism. When actuator 515 is actuated, actuator shaft 510 is moved upward toward needle 210. In turn, mechanical linkage interface 545, which is mated with plunger interface 420, moves plunger 415 upward toward needle 210. A substance located in dispensing chamber 405 is then expelled through needle 210.

In addition, controller 305 controls the operation of temperature control device 450. Temperature control device 450 is adapted to heat and/or cool dispensing chamber housing 425 and its contents. Since dispensing chamber housing 425 is at least partially thermally conductive, heating or cooling dispensing chamber housing 425 heats or cools a substance located in dispensing chamber 405. Temperature information can be transferred from thermal sensor 460 through interface 530, tip interface connector 453, limited reuse assembly interface connector 553, and interface 535 back to controller 305. This temperature information can be used to control the operation of temperature control device 450. When temperature control device 450 is a heater, controller 305 controls the amount of current that is sent to temperature control device 450. The more current sent to temperature control device 450, the hotter it gets. In such a manner, controller 305 can use a feed back loop utilizing information from thermal sensor 460 to control the operation of temperature control device 450. Any suitable type of control algorithm, such as a proportional integral derivative (PID) algorithm, can be used to control the operation of temperature control device 450.

A substance to be delivered into an eye, typically a drug suspended in a phase transition compound, is located in dispensing chamber 405. In this manner, the drug and phase transition compound are contacted by the inner surface of dispensing chamber housing 425. The phase transition compound is in a solid or semi-solid state at lower temperatures and in a more liquid state at higher temperatures. Such a compound can be heated by the application of current to temperature control device 450 to a more liquid state and injected into the eye where it forms a bolus that erodes over time.

In one embodiment of the present invention, the substance located in dispensing chamber 405 is a drug that is preloaded into the dispensing chamber. In such a case, tip segment 205 is appropriate as a single use consumable product. Such a disposable product can be assembled at a factory with a dosage of a drug installed.

While shown as a two-piece device, the injection system of FIG. 4 may be a single piece device. In such a case, the tip segment is integrated into the limited reuse assembly to form a single medical device.

Figure 5:
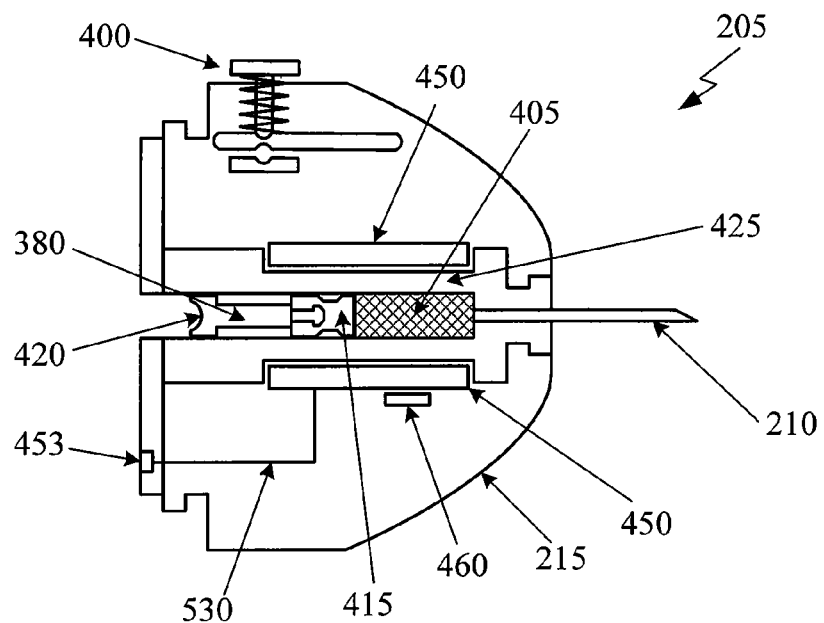
FIG. 5 is an exploded cross section view of a tip segment for an ophthalmic medical device according to an embodiment of the present invention.

FIG. 5 is an exploded cross section view of a tip segment for an ophthalmic medical device according to an embodiment of the present invention. In FIG. 5, tip segment 205 includes dispensing chamber housing 425, tip segment housing 215, thermal sensor 460, needle 210, dispensing chamber 405, plunger 415, plunger shaft 380, plunger interface 420, temperature control device 450, interface 530, tip interface connector 453, and temperature release mechanism 400.

In the embodiment of FIG. 5, temperature control device 450 is activated to bring a substance in dispensing chamber 405 to within a proper temperature range. Thermal sensor 460 provides temperature information to controller 305 (not shown) to control temperature control device 450. After the substance has reached the proper temperature, temperature release mechanism 400 is actuated to drive plunger toward needle 210 to dispense a substance contained in dispensing chamber 405. Temperature release mechanism 400 can only be activated when the substance is in the proper temperature range. In this manner, the substance in dispensing chamber 405 is delivered only when it is in the proper temperature range.

In addition, the embodiment of FIG. 5 includes a plunger shaft 380 that is connected to plunger 415. In this embodiment, plunger 415 may be over-molded onto plunger shaft 380. Plunger shaft 380 is generally cylindrical in shape with a middle diameter that is less than a diameter on its distal and proximal ends. Plunger interface 420 is a surface on the proximal end of plunger shaft 380. Plunger shaft 380 is typically made of a rigid material such as stainless steel. Plunger 415 is made of a rubber or polymer material. In another embodiment of the present invention, the distal end of plunger shaft 380 has a lip over which plunger 415 can be applied. Plunger 415 can be press-fitted onto plunger shaft 380 and is retained in place by a lip on the distal end of plunger shaft 380. This allows for easier assembly. Instead of over molding plunger 415 onto a shaft, plunger 415 can be manufactured as a separate part and pushed onto the distal end of plunger shaft 380. Plunger interface 420 can be of any suitable shape.

As seen in FIG. 5, temperature release mechanism may be incorporated into tip segment 205, in which case it is not present in limited reuse assembly 250. In this manner, temperature release mechanism may be located in tip segment 205 or in limited reuse assembly 250. When a single integrated unit (integrating tip segment 205 and limited reuse assembly 250 into a single device), temperature release mechanism may be located in the integrated unit.

Temperature release mechanism 400 may be located such that it operates to allow dispensing of the substance only when the substance is in the proper temperature range. Since different materials can be used to make temperature release mechanism 400 (as described below), the location of temperature release mechanism is dependent on its structure and the materials used to make it. For example, when temperature release mechanism 400 includes a Nitinol member (as described below), temperature release mechanism 400 should be positioned such that it can be activated only when the substance is in the proper temperature range. In this case, temperature release mechanism 400 may be placed near temperature control device 450 and dispensing chamber housing 425, so that heat produced by temperature control device 450 and conducted by dispensing chamber housing 425 alters the shape of the Nitinol member in such a way as to permit dispensing of the substance when it is in the proper temperature range.

Figures 6A, 6B:
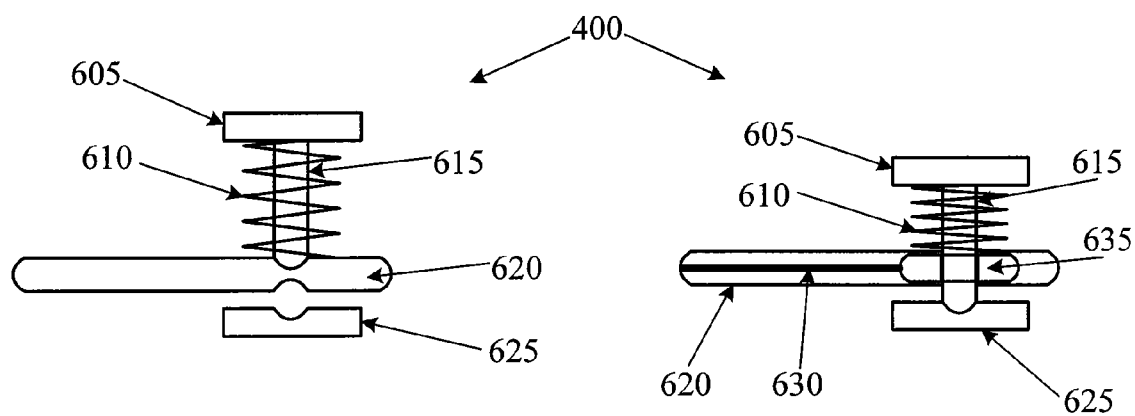
FIGS. 6A and 6B are exploded cross section views of temperature release mechanism according to the principles of the present invention.

FIGS. 6A and 6B are exploded cross section views of a temperature release mechanism according to the principles of the present invention. Temperature release mechanism 400 includes button 605, spring 610, shaft 615, locking mechanism 620, and triggering device 625. In FIG. 6B, shape memory alloy member 630 and disk 635 are also depicted.

Button 605 is located on top of shaft 615. Shaft 615 is located in a notch in locking mechanism 620. Spring 610 biases shaft 615 upward and away from locking mechanism 620. Spring 610 also provides some resistance to button 605 when it is pushed. Triggering device 625 is located below locking mechanism 620. As shown in FIG. 6B, shape memory alloy member 630 and disk 635 are located in locking mechanism 620. Shape memory alloy member 630 is connected to disk 635. In one embodiment consistent with the principles of the present invention, shape memory alloy member 630 and disk 635 are made out of the same shape memory alloy material.

Triggering device 625 is a switch, contact, or other similar device that can initiate the actuation of substance delivery. For example, triggering device 625 may be a switch that activates actuator 515 to drive actuator shaft 510 and mechanical linkage mechanism 545 toward needle 210 to deliver the substance from dispensing chamber 405.

In FIG. 6B, shape memory alloy member 630 is made of a shape memory alloy ("SMA"). Shape memory alloys, such as various Nitinol (a nickel-titanium alloy) alloys, hold a deformed shape at room temperature. When heated to a higher temperature, the SMA reverts to its non-deformed shape. In other words, a shape memory alloy (also known as a smart alloy or memory metal) is a metal that "remembers" its geometry. After an SMA has been deformed from its original atomic configuration, it regains its original geometry by itself during heating. These properties are due to a temperature-dependent martensitic phase transformation from a low-symmetry to a highly symmetric crystallographic structure. Those crystal structures are known as martensite and austenite. The three main types of SMA are copper-zinc-aluminum, copper-aluminum-nickel, and nickel-titanium (Ni—Ti) alloys. The temperatures at which the SMA changes its crystallographic structure are characteristic of the alloy, and can be tuned by varying the elemental ratios.

For a shape memory alloy member 630 made out of Nitinol, the Nitinol is in a deformed shape at room temperature. In this deformed shape, the Nitinol has a martenistic crystal structure. In this deformed shape, when shape memory alloy member 630 is a wire-type structure, it has first length. As the temperature of shape memory alloy member 630 rises, its shape changes. When the temperature of shape memory alloy member 630 reaches 60 or 70 degrees Celsius, the Nitinol will revert to its non-deformed shape. In this process, the Nitinol changes from a martenistic crystal structure to an austenic crystal structure. In this non-deformed shape, when shape memory alloy member 630 is a wire-type structure, it has a second length. As the temperature of shape memory alloy member 630 increases, the transition from the first length to the second length can be gradual.

In FIG. 6B, shape memory alloy member 630 is at the desired temperature range. In this temperature range, shaft 615 is able to traverse locking mechanism 620 through an opening in disk 635. In this embodiment, shape memory alloy member 630 is a wire-type structure. However, shape memory alloy member 630 may be any convenient structure, such as a coil. In other embodiments, shape memory alloy member 630 is toroidal in shape, in which case the opening in the toroid can be varied by varying its temperature.

In operation, when shape memory alloy member 630 in locking mechanism 620 is at room temperature, shaft 615 is not able to contact triggering device 625 (as shown in FIG. 6A). As shape memory alloy member 630 is heated, its shape changes. As its shape changes, disk 635 slides in locking mechanism 620. When shape memory alloy member 630 reaches the proper temperature range, disk 635 is located such that shaft 615 is able to pass through it and contact triggering device 625.

FIGS. 7A-7H are exploded cross section views of a portion of a temperature release mechanism according to the principles of the present invention. FIGS. 7A-7D are top cross section views, and FIGS. 7E-7H are side cross section views.

Figure 7A:
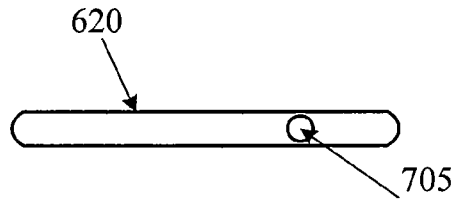
FIGS. 7A-7H are exploded cross section views of a portion of a temperature release mechanism according to the principles of the present invention.
Figure 7E:
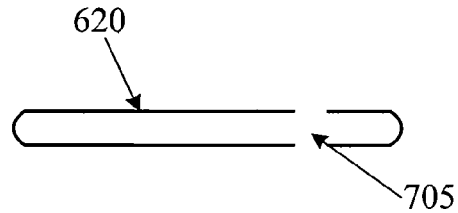

FIGS. 7A and 7E are top and side cross section views of locking mechanism 620. An opening 705 is shown. Locking mechanism 620 is hollow and, in this case, tubular. Shaft 615 is located above opening 705, such that it can pass through opening 705 to activate triggering device 625 (as shown in FIG. 6B).

Figure 7B:
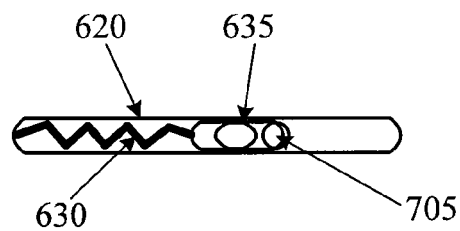
Figure 7F:
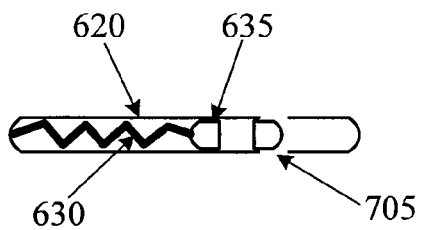

In FIGS. 7B and 7F, shape memory alloy member 630 is at room temperature or in a low temperature range. Shape memory alloy member 630 is shown as a coil. In this position, disk 635 blocks opening 705, thus preventing shaft 615 from contacting triggering device 625. The opening in disk 635 is not aligned with opening 705.

Figure 7C:
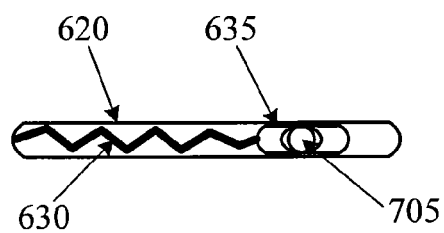
Figure 7G:
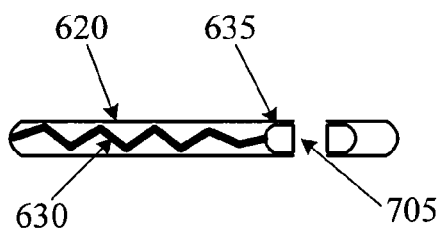

In FIGS. 7C and 7G, shape memory alloy member 630 is in a proper temperature range. In this position, the opening in disk 635 is aligned with opening 705, thus allowing shaft 615 to pass through locking mechanism 620 and contact triggering device 625. In this manner, when the substance in the dispensing chamber is in the proper temperature range (and the opening in disk 635 is aligned with opening 705), actuator 515 can be activated to deliver the substance into an eye.

Figure 7D:
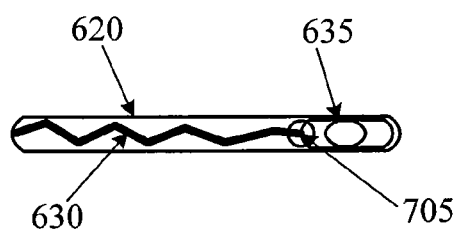
Figure 7H:
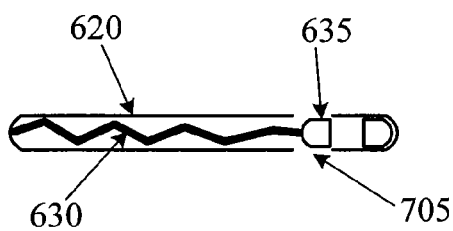

In FIGS. 7D and 7H, shape memory alloy member 630 is in a high temperature range. In this position, disk 635 blocks opening 705, thus preventing shaft 615 from contacting triggering device 625. The opening in disk 635 is not aligned with opening 705.

When temperature release mechanism 400 is located near dispensing chamber housing 425 (or temperature control device 450), shape memory alloy member 630 can be altered by the heat produced by temperature control device 450 (when it is a heater). As temperature control device 450 heats up, a substance located in dispensing chamber 405 also heats up. This in turn causes shape memory alloy member 630 to change shape and move disk 635. When the substance is in the proper temperature range, shape memory alloy member 630 has changed shape so that the opening in disk 635 is aligned with opening 705 in locking mechanism 620. When these two openings are aligned, shaft 615 can pass through locking mechanism 620 and disk 635 to contact triggering device 625. In this case, when button 605 is pushed, the substance (which is in the correct temperature range) is delivered into an eye. If the substance is too hot, then the button cannot be depressed as the opening in disk 635 is not aligned with the opening 705 in locking mechanism 620. In this manner, the actuation of drug delivery device only occurs when the drug is in the proper temperature range.

From the above, it may be appreciated that the present invention provides an improved system for delivering precise volumes of a substance into an eye. The present invention provides a temperature release mechanism that ensures that a substance is delivered into an eye only when it is in a proper temperature range. In one embodiment, a disposable tip segment that interfaces with a limited reuse assembly is employed. In another embodiment, a single unit is employed. The present invention is illustrated herein by example, and various modifications may be made by a person of ordinary skill in the art.

While the present invention is described in the context of a single-use drug delivery device, the present invention encompasses any single-use medical device. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic injection device comprising:
a dispensing chamber housing having an inner surface and an outer surface, the inner surface partially defining a dispensing chamber for holding a quantity of a substance;
a plunger engaged with the inner surface of the dispensing chamber housing, the plunger capable of sliding in the dispensing chamber housing, the plunger fluidly sealed to the inner surface of the dispensing chamber housing;
a temperature control device at least partially surrounding the dispensing chamber housing, the temperature control device for altering a temperature of the substance in the dispensing chamber;
a power source for providing power to the temperature control device;
a controller for controlling the temperature control device;
an actuator for driving the plunger; and
a temperature release mechanism that activates the actuator when the substance is in a temperature range; the temperature release mechanism comprising a shape memory alloy member, a disk with an aperture, and a triggering device, the shape memory alloy member coupled to the disk so that as the shape memory alloy member changes shape the disk is moved into a position to allow the triggering device to be activated.

2. The device of claim 1 further comprising:
a thermal sensor located near the dispensing chamber housing, the thermal sensor for measuring a temperature.

3. The device of claim 2 wherein the controller uses the measured temperature to control the temperature control device.

4. The device of claim 1 wherein the temperature release mechanism is in a locked position when the substance is outside the temperature range.

5. The device of claim 1 wherein the temperature release mechanism further comprises:
a button rigidly connected to a shaft; and
a spring biasing the button.

6. The device of claim 1 wherein when the substance is in the proper temperature range, the shape memory alloy member is in a configuration that permits activation of the actuator.

7. The device of claim 1 wherein the temperature control device is a heater.

8. The device of claim 1 wherein the substance is a drug for treating a condition of the eye.

9. The device of claim 1 further comprising:
a needle fluidly coupled to the dispensing chamber.

10. The device of claim 1 wherein the power source is a rechargeable battery.

* * * * *